United States Patent
Hataoka

(10) Patent No.: US 8,785,143 B2
(45) Date of Patent: *Jul. 22, 2014

(54) METHOD FOR IMMOBILIZING STREPTAVIDIN ON A SELF-ASSEMBLED MONOLAYER

(71) Applicant: Panasonic Corporation, Osaka (JP)

(72) Inventor: Yukari Hataoka, Osaka (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/629,121

(22) Filed: Sep. 27, 2012

(65) Prior Publication Data

US 2013/0023059 A1 Jan. 24, 2013

Related U.S. Application Data

(63) Continuation of application No. PCT/JP2011/001185, filed on Mar. 1, 2011.

(30) Foreign Application Priority Data

Aug. 30, 2010 (JP) ................ 2010-191796

(51) Int. Cl.
| | |
|---|---|
| G01N 33/53 | (2006.01) |
| G01N 33/544 | (2006.01) |
| G01N 33/543 | (2006.01) |
| A61K 39/00 | (2006.01) |

(52) U.S. Cl.
CPC .... G01N 33/54353 (2013.01); *A61K 2039/625* (2013.01); *G01N 33/54306* (2013.01); *G01N 33/53* (2013.01); *C07K 2319/20* (2013.01); *G01N 2610/00* (2013.01)

USPC .............................. 435/7.5; 435/7.1; 436/528

(58) Field of Classification Search
None
See application file for complete search history.

(56) References Cited

U.S. PATENT DOCUMENTS

| | | | |
|---|---|---|---|
| 5,137,804 | A | 8/1992 | Greene et al. |
| 5,391,478 | A | 2/1995 | Greene et al. |
| 5,969,758 | A | 10/1999 | Sauer et al. |
| 6,037,577 | A | 3/2000 | Tanaka et al. |
| 6,061,093 | A | 5/2000 | Yonemoto |

(Continued)

FOREIGN PATENT DOCUMENTS

| | | |
|---|---|---|
| EP | 0 865 197 A2 | 9/1998 |
| EP | 908957 A2 | 4/1999 |

(Continued)

OTHER PUBLICATIONS

Besselink et al. N-hydroxysuccinimide-activated glycine-sepharose. Applied Biochemistry and Biotechnology 2003, vol. 43, pp. 227-246.*

(Continued)

*Primary Examiner* — Shafiqul Haq
(74) *Attorney, Agent, or Firm* — McDermott Will & Emery LLP

(57) ABSTRACT

Provided are a method for increasing an amount of streptavidin to be immobilized on the self-assembled monolayer and a sensor which comprises streptavidin immobilized with the method. The method of the current technology is characterized by that one molecule of an amino acid is interposed between the self-assembled monolayer and the molecule of streptavidin.

12 Claims, 3 Drawing Sheets

(56) References Cited

U.S. PATENT DOCUMENTS

| | | | |
|---|---|---|---|
| 6,115,066 A | 9/2000 | Gowda et al. | |
| 6,235,535 B1 | 5/2001 | Keinanen et al. | |
| 6,344,877 B1 | 2/2002 | Gowda et al. | |
| 6,366,321 B1 | 4/2002 | Yonemoto | |
| 6,406,921 B1* | 6/2002 | Wagner et al. | 436/518 |
| 6,475,808 B1 | 11/2002 | Wagner et al. | |
| 6,576,478 B1 | 6/2003 | Wagner et al. | |
| 6,582,969 B1 | 6/2003 | Wagner et al. | |
| 6,596,545 B1 | 7/2003 | Wagner et al. | |
| 6,650,369 B2 | 11/2003 | Koizumi et al. | |
| 6,682,942 B1 | 1/2004 | Wagner et al. | |
| 6,791,613 B2 | 9/2004 | Shinohara et al. | |
| 7,030,922 B2 | 4/2006 | Sakuragi | |
| 7,110,030 B1 | 9/2006 | Kochi et al. | |
| 7,116,365 B1 | 10/2006 | Ueno et al. | |
| 7,277,130 B2 | 10/2007 | Korthout et al. | |
| 7,283,168 B2 | 10/2007 | Watanabe | |
| 7,317,483 B2 | 1/2008 | Tanimoto | |
| 7,375,753 B2 | 5/2008 | Mabuchi | |
| 7,714,920 B2 | 5/2010 | Inagaki et al. | |
| 2002/0110932 A1 | 8/2002 | Wagner et al. | |
| 2002/0115225 A1 | 8/2002 | Wagner et al. | |
| 2003/0137594 A1 | 7/2003 | Koizumi et al. | |
| 2003/0138973 A1 | 7/2003 | Wagner et al. | |
| 2004/0027471 A1 | 2/2004 | Koseki et al. | |
| 2004/0175300 A1 | 9/2004 | Indermuhle et al. | |
| 2004/0197931 A1 | 10/2004 | Indermuhle et al. | |
| 2004/0251396 A1 | 12/2004 | Koyama | |
| 2005/0083408 A1 | 4/2005 | Mabuchi | |
| 2005/0128326 A1 | 6/2005 | Korthout et al. | |
| 2005/0281816 A1 | 12/2005 | Lamping et al. | |
| 2006/0001751 A1 | 1/2006 | Abe et al. | |
| 2009/0011952 A1 | 1/2009 | Gau | |
| 2009/0042744 A1 | 2/2009 | Wagner et al. | |
| 2009/0047685 A1 | 2/2009 | Kohno et al. | |
| 2009/0047695 A1 | 2/2009 | Wagner et al. | |
| 2009/0202580 A1 | 8/2009 | Uggeri et al. | |
| 2009/0325262 A1 | 12/2009 | Hodneland et al. | |
| 2010/0113476 A1* | 5/2010 | Chen et al. | 514/254.08 |
| 2010/0233827 A1 | 9/2010 | Kusaki et al. | |
| 2012/0238036 A1* | 9/2012 | Hataoka | 436/501 |
| 2013/0029364 A1 | 1/2013 | Hataoka | |

FOREIGN PATENT DOCUMENTS

| | | |
|---|---|---|
| GB | 2 347 212 A | 8/2000 |
| JP | 01-209370 A | 8/1989 |
| JP | 07-113637 B | 12/1995 |
| JP | 9-247537 A | 9/1997 |
| JP | 10-93066 A | 4/1998 |
| JP | 11-014627 A | 1/1999 |
| JP | 11-112018 A | 4/1999 |
| JP | 2000-515965 A | 11/2000 |
| JP | 2001-045375 A | 2/2001 |
| JP | 2001-305139 A | 10/2001 |
| JP | 2002-511215 A | 4/2002 |
| JP | 2002-520618 A | 7/2002 |
| JP | 2002-520621 A | 7/2002 |
| JP | 2002-237584 A | 8/2002 |
| JP | 2003-230055 A | 8/2003 |
| JP | 2005-509737 A | 4/2005 |
| JP | 2006-502719 A | 1/2006 |
| JP | 2006-166837 A | 6/2006 |
| JP | 2006-208012 A | 8/2006 |
| JP | 2006-266707 A | 10/2006 |
| JP | 2007-528850 A | 10/2007 |
| JP | 2007-298334 A | 11/2007 |
| JP | 2009-222401 A | 10/2009 |
| JP | 2009-541259 A | 11/2009 |
| JP | 2010-117140 A | 5/2010 |
| JP | 2010-237191 A | 10/2010 |
| JP | 2010-532475 A | 10/2010 |
| WO | 89/11100 A1 | 11/1989 |
| WO | 98/00714 A1 | 1/1998 |
| WO | 98/56170 A1 | 12/1998 |
| WO | 00/04390 A2 | 1/2000 |
| WO | WO-00/04382 A1 | 1/2000 |
| WO | 03/018854 A2 | 3/2003 |
| WO | 03/069897 A1 | 8/2003 |
| WO | WO-2005/018413 A2 | 3/2005 |
| WO | 2007/063616 A1 | 6/2007 |
| WO | 2009/005567 A1 | 1/2009 |
| WO | 2011/089903 A1 | 7/2011 |
| WO | 2012/029202 A1 | 3/2012 |
| WO | 2012/053138 A1 | 4/2012 |
| WO | 2012/168988 A1 | 12/2012 |
| WO | 2013/005269 A1 | 1/2013 |

OTHER PUBLICATIONS

Diamandis et al. The biotin-(strept)avidin system: principles and applications in biotechnology. Clin. Chem. 1991, vol. 37, No. 5, pp. 625-636.*

International Search Report mailed Mar. 29, 2011 issued in corresponding International Application No. PCT/JP2011/001185.

Chinese Search Report issued in corresponding Chinese Application No. 201180037848.6, dated Mar. 3, 2014, with English translation.

Gooding et al., "Amperometric biosensor with enzyme amplification fabricated using self-assembled monolayers of alkanethiols: the influence of the spatial distribution of the enzymes", Electrochemistry Communications, vol. 2, No. 4, Apr. 1, 2000, pp. 217-221.

International Search Report issued in International Application No. PCT/JP2011/004127 issued on Aug. 16, 2011.

International Search Report issued in International Patent Application No. PCT/JP2011/007239 dated Feb. 7, 2012.

International Search Report issued in International Application No. PCT/JP2011/007238 with Date of mailing Feb. 7, 2012.

Besselink et al., "N-hydroxysuccinimide-activated glycine-sepharose," Applied Biochemistry and Biotechnology 2003, vol. 43, pp. 227-246.

Diamandis et al., "The biotin-(strept)avidin system: principles and applications in biotechnology," Clin. Chem. 1991, vol. 37, No. 5, pp. 625-636.

International Search Report issued in International Application No. PCT/JP2011/005037 with Date of mailing Oct. 11, 2011, with English Translation.

Kondo et al., "Plasma-Assisted Immobilization of Heparin onto Low-Density Polyethylene Surface," Chem. Pharm. Bull., 2008, vol. 56, No. 7, p. 921-925.

Shriver-Lake et al., Antibody Immobilization Using Heterobifunctional Crosslinkers, Biosensors & Bioelectronics, 1997, vol. 12, No. 11, p. 1101-1106.

Notice of Allowance issued in U.S. Appl. No. 13/483,840 dated Oct. 31, 2013.

Final Office Action issued in U.S. Appl. No. 13/483,840 dated Sep. 13, 2013.

Non-Final Office Action issued in U.S. Appl. No. 13/483,840 dated Feb. 27, 2013.

Non-Final Office Action issued in U.S. Appl. No. 13/483,840 dated Sep. 27, 2012.

International Search Report issued in International Application No. PCT/JP2011/000268 with Date of mailing Apr. 5, 2011.

* cited by examiner

Related Art

Related Art

METHOD FOR IMMOBILIZING STREPTAVIDIN ON A SELF-ASSEMBLED MONOLAYER

CROSS-REFERENCE TO RELATED APPLICATIONS

This is a continuation of International Application No. PCT/JP2011/001185, with an international filing date of Mar. 1, 2011, which claims priority of Japanese Patent Application No. 2010-191796, filed on Aug. 30, 2010, the contents of which are hereby incorporated by reference.

TECHNICAL FIELD

The disclosure herein relates to a method for immobilizing streptavidin on a self-assembled monolayer.

BACKGROUND ART

A biosensor is used to detect or quantify a target substance contained in a sample. A high affinity between streptavidin and biotin may be used in the biosensor. Specifically, streptavidin is immobilized on the biosensor. The target substance is modified with a biotin molecule. When the target substance is supplied to the biosensor, the target substance is immobilized on the biosensor due to the high affinity between streptavidin and biotin.

Patent Document 1 discloses a prior biosensor utilizing the high affinity between streptavidin and biotin. FIG. 2 shows a biosensor disclosed in FIG. 7 of the Patent Document 1.

According to the description regarding FIG. 7 of the Patent Document 1, the biosensor is used for screening of biomoleculer activity. The biosensor comprises a monolayer 7, an affinity tag 8, an adaptor molecule 9, and a protein 10. The monolayer 7 is composed of a self-assembled monolayer represented by chemical formula: X—R—Y (see Page 24 lines 23-26, Page 25 lines 3-20, Page 25 line 27-Page 26 line 13, and Page 26 lines 14-22 of Patent Document 1). Examples of X, R, and Y are HS—, an alkane, and a carboxyl group, respectively (see Page 25 lines 3-20, Page 25 line 27-Page 26 line 13, and Page 28 lines 21-23 of Patent Document 1).

The affinity tag 8 and the adaptor molecule 9 may be composed of streptavidin and a biotin molecule, respectively (see Page 36 lines 3-5 of Patent Document 1).

CITATION LIST

Patent Literature

[PTL 1]
WO00/04382, which corresponds to Japanese Unexamined Patent Application Publication (Translation of PCT Application) No. 2002-520618 (see paragraph [0080], [0082], [0084], [0085], [0109] and [0119])

SUMMARY OF INVENTION

Technical Problem

In order to improve the detection sensitivity or the quantification accuracy of the target substance, it is required to increase an amount of streptavidin to be immobilized on the biosensor.

The present inventor has discovered that the amount of immobilized streptavidin per unit area was significantly increased by binding one molecule amino acid to a self-assembled monolayer and then immobilizing streptavidin. The technologies herein have been provided on the basis of the discovery.

Thus, provided herein are a method for increase an amount of streptavidin to be immobilized on the self-assembled monolayer, and a sensor with the streptavidin immobilized with the same method.

Solution to Problem

The following items [1] to [22] solve the above problem(s).
[1] A method for immobilizing a streptavidin on a self-assembled monolayer, comprising the following steps (a) and (b) in this order:
a step (a) of preparing a substrate comprising one molecule of an amino acid and the self-assembled monolayer, wherein,
the one molecule of the amino acid is bound to the self-assembled monolayer with a peptide bond represented by the following chemical formula (I):

[Chem. 1]

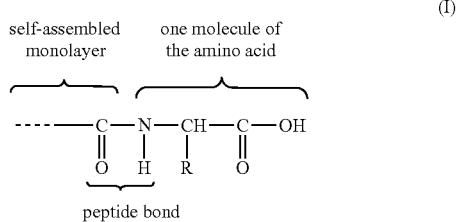

(wherein R represents a side chain of the one molecule of the amino acid)
the one molecule of the amino acid is selected from the twenty kinds of amino acids consisting of Cysteine, Lysine, Histidine, Phenylalanine, Tyrosine, Glycine, Asparagine, Methionine, Serine, Tryptophan, Leucine, Glutamine, Alanine, Isoleucine, Threonine, Proline, Glutamate, Aspartate, Arginine, and Valine, and
a step (b) of supplying the streptavidin to the substrate to form a peptide bond represented by the following chemical formula (II) between the carboxyl group of the one molecule of the amino acid and the amino group of the streptavidin.

[Chem. 2]

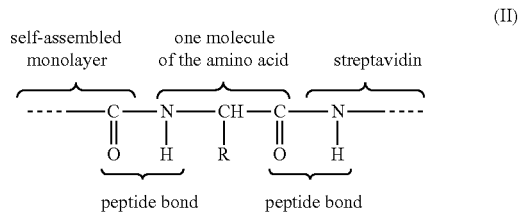

(wherein R represents a side chain of the one molecule of the amino acid)
[2] A method according to item [1], wherein the step (a) comprises the following steps (a1) and (a2):
a step (a1) of preparing a substrate comprising a self-assembled monolayer on the surface thereof, the self-assembled monolayer having a carboxylic acid at one end, and
a step (a2) of supplying the one molecule of the amino acid to form a peptide bond represented by the chemical formula (I) between the carboxylic group of the one end of the self-assembled monolayer and the amino group of the one molecule of the amino acid.

[3] A method according to item [1], further comprising the following step (ab) between the step (a) and the step (b):

a step (ab) of activating the carboxyl group of the one molecule of the amino acid with a mixture of N-Hydroxysuccinimide and 1-ethyl-3-(3-dimethylaminopropyl)carbodiimide hydrochloride.

[4] A method according to item [2], further comprising the following step (a1a) between the step (a1) and the step (a2):

a step (a1a) of activating the carboxyl group of the self-assembled monolayer with a mixture of N-Hydroxysuccinimide and 1-ethyl-3-(3-dimethylaminopropyl)carbodiimide hydrochloride.

[5] A method according to item [1], wherein the chemical formula (II) is represented by the following chemical formula (III).

[Chem. 3]

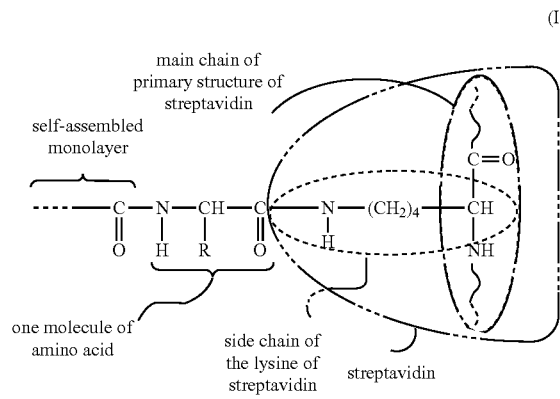

(III)

(wherein R represents a side chain of the one molecule of the amino acid)

[6] A method according to item [1], wherein the one molecule of the amino acid is selected from the group consisting of Lysine, Histidine, Phenylalanine, Cysteine, Glycine, Methionine, Glutamate, Tyrosine, Alanine, Serine, Aspartate, Asparagine, Leucine, Tryptophan, Threonine, Isoleucine, and Valine.

[7] A method according to item [1], wherein the one molecule of the amino acid is selected from the group consisting of Lysine, Histidine, Phenylalanine, Cysteine, Glycine, Methionine, Glutamate, Tyrosine, Alanine, Serine, Aspartate, Asparagine, Leucine, and Tryptophan.

[8] A method according to item [1], wherein the one molecule of the amino acid is selected from the group consisting of Lysine, Histidine, Phenylalanine, Cysteine, Glycine, Methionine, Glutamate, Tyrosine, Alanine, Serine, Aspartate, and Asparagine.

[9] A method according to item [1], wherein the one molecule of the amino acid is selected from the group consisting of Lysine, Histidine, Phenylalanine, Cysteine, Glycine, Methionine, Glutamate, Tyrosine, Alanine, and Serine.

[10] A sensor comprising a self-assembled monolayer, one molecule of an amino acid, and a streptavidin, wherein, the one molecule of the amino acid is interposed between the self-assembled monolayer and the streptavidin, the streptavidin is bound to the self-assembled monolayer with two peptide bonds represented by the following chemical formula (II),

[Chem. 2]

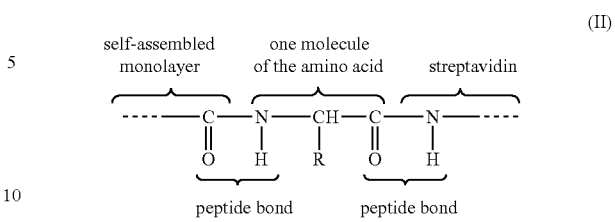

(II)

(wherein R represents a side chain of the one molecule of the amino acid) the one molecule of the amino acid is selected from the twenty kinds of amino acids consisting of Cysteine, Lysine, Histidine, Phenylalanine, Tyrosine, Glycine, Asparagines, Methionine, Serine, Tryptophan, Leucine, Glutamine, Alanine, Isoleucine, Threonine, Pro line, Glutamate, Aspartate, Arginine, and Valine.

[11] A method according to item [10], wherein the chemical formula (II) is represented by the following chemical formula (III).

[Chem. 3]

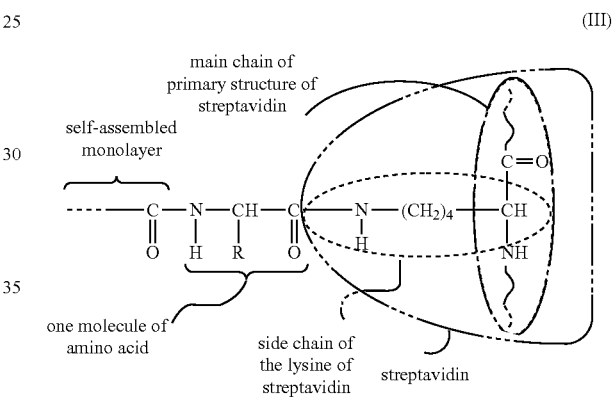

(III)

(wherein R represents a side chain of the one molecule of the amino acid)

[12] A sensor according to item [10], wherein the one molecule of the amino acid is selected from the group consisting of Lysine, Histidine, Phenylalanine, Cysteine, Glycine, Methionine, Glutamate, Tyrosine, Alanine, Serine, Aspartate, Asparagine, Leucine, Tryptophan, Threonine, Isoleucine, and Valine.

[13] A sensor according to item [10], wherein the one molecule of the amino acid is selected from the group consisting of Lysine, Histidine, Phenylalanine, Cysteine, Glycine, Methionine, Glutamate, Tyrosine, Alanine, Serine, Aspartate, Asparagine, Leucine, and Tryptophan.

[14] A sensor according to item [10], wherein the one molecule of the amino acid is selected from the group consisting of Lysine, Histidine, Phenylalanine, Cysteine, Glycine, Methionine, Glutamate, Tyrosine, Alanine, Serine, Aspartate, and Asparagine.

[15] A sensor according to item [10], wherein the one molecule of the amino acid is selected from the group consisting of Lysine, Histidine, Phenylalanine, Cysteine, Glycine, Methionine, Glutamate, Tyrosine, Alanine, and Serine.

[16] A method for detecting or quantifying a target substance contained in a sample with a sensor, comprising the following steps (a) to (c) in this order, a step (a) of preparing the sensor comprising a self-assembled monolayer, one molecule of an amino acid, and a streptavidin, wherein, the one molecule of the amino acid is interposed between the self-assembled monolayer and the streptavidin, the streptavidin is bound to the self-assembled monolayer with two peptide bonds represented by the following chemical formula (II),

[Chem. 2]

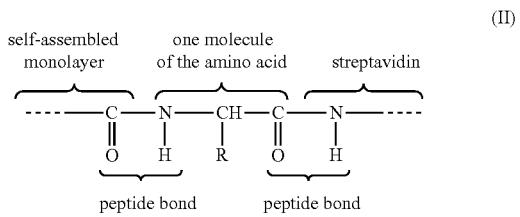

(II)

(wherein R represents a side chain of the one molecule of the amino acid)

the one molecule of the amino acid is selected from the twenty kinds of amino acids consisting of Cysteine, Lysine, Histidine, Phenylalanine, Tyrosine, Glycine, Asparagine, Methionine, Serine, Tryptophan, Leucine, Glutamine, Alanine, Isoleucine, Threonine, Proline, Glutamate, Aspartate, Arginine, and Valine, a step (b) of supplying the sample to the sensor to cause the target substance to be bound to streptavidin, and a step (c) of detecting or quantifying the target substance contained in the sample from the captured target substance or the amount thereof.

[17] A method according to item [16], wherein, the step (b) comprises the following steps (b1) and (b2):

a step (b1) of binding an antibody to the streptavidin, the antibody modified with biotin, and a step (b2) of binding the target substance to the antibody.

[18] A method according to item [16], wherein the chemical formula (II) is represented by the following chemical formula (III).

[Chem. 3]

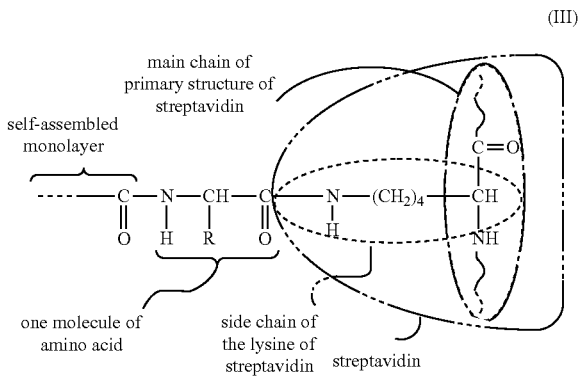

(III)

(wherein R represents a side chain of the one molecule of the amino acid)

[19] A method according to item [16], wherein the one molecule of the amino acid is selected from the group consisting of Lysine, Histidine, Phenylalanine, Cysteine, Glycine, Methionine, Glutamate, Tyrosine, Alanine, Serine, Aspartate, Asparagine, Leucine, Tryptophan, Threonine, Isoleucine, and Valine.

[20] A method according to item [16], wherein the one molecule of the amino acid is selected from the group consisting of Lysine, Histidine, Phenylalanine, Cysteine, Glycine, Methionine, Glutamate, Tyrosine, Alanine, Serine, Aspartate, Asparagine, Leucine, and Tryptophan

[21] A method according to item [16], wherein the one molecule of the amino acid is selected from the group consisting of Lysine, Histidine, Phenylalanine, Cysteine, Glycine, Methionine, Glutamate, Tyrosine, Alanine, Serine, Aspartate, and Asparagine.

[22] A method according to item [16], wherein the one molecule of the amino acid is selected from the group consisting of Lysine, Histidine, Phenylalanine, Cysteine, Glycine, Methionine, Glutamate, Tyrosine, Alanine, and Serine.

Advantageous Effect of Invention

The exemplary embodiments achieve extreme increase of the amount of the streptavidin to be immobilized per unit area.

DESCRIPTION OF EMBODIMENTS

An exemplary embodiment is described below with reference to FIG. 1.

Embodiment 1

Figure 1:
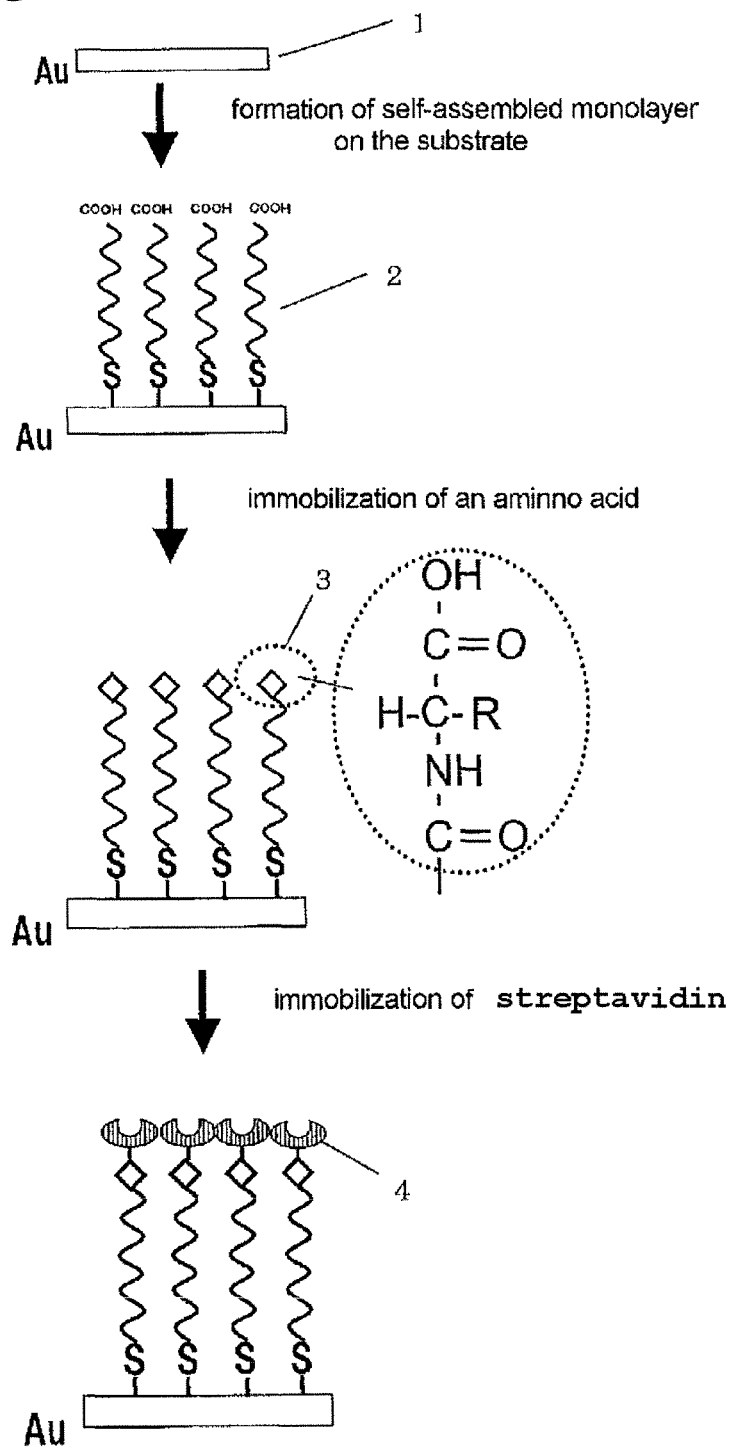
FIG. 1 shows a schematic view of a method according to an exemplary embodiment.
Figure 2:
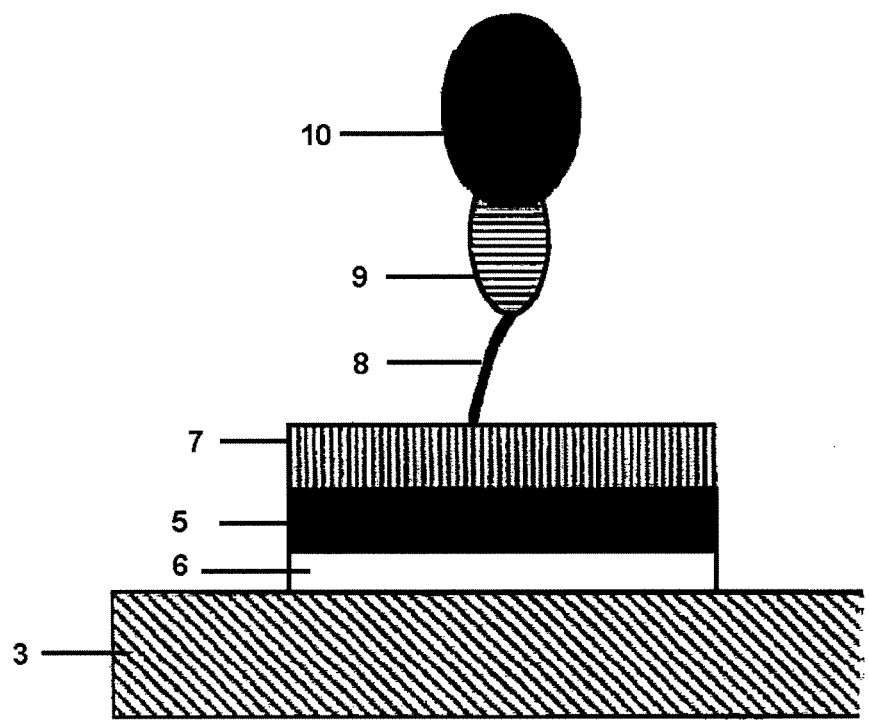
FIG. 2 is FIG. 7 of Patent Document 1.

FIG. 1 shows a method according to an exemplary embodiment for immobilizing a streptavidin on a self-assembled monolayer.

Preferably, a substrate 1 is a gold substrate. An example of the gold substrate is a substrate comprising gold on its surface. Specifically, the gold substrate may be formed by a sputtering gold on the surface of glass, plastic, or silicon dioxide ($SiO_2$).

First, the substrate 1 is immersed into a solvent containing an alkanethiol. Preferably, the substrate is washed before the immersing. The alkanethiol has a carboxyl group at the end thereof. As the alkanethiol, a primary alkanethiol having carbon number within the range from 6 to 18 can be employed preferably. Thus, a self-assembled monolayer 2 is formed on the substrate 1.

A preferred concentration of the alkanethiol is approximately 1 to 10 mM. The solvent is not limited as long as it dissolves the alkanethiol. Examples of the preferred solvent are ethanol, DMSO (dimethyl sulfoxide), and dioxane. The preferred immersing period is approximately 12 to 48 hours.

Next, an amino acid 3 is supplied to the self-assembled monolayer 2. The carboxyl group (—COOH), which locates at the top end of the self-assembled monolayer 2, reacts with an amino group (—$NH_2$) of the amino acid 3 to form a peptide bond represented by the following the chemical formula (I).

[Chem. 1]

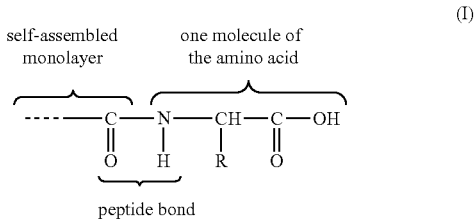

(I)

(wherein R represents side chain of the one molecule of the amino acid)

In the chemical formula (I), one molecule of the amino acid 3 binds to the self-assembled monolayer 2.

The amino acid 3 is selected from twenty kinds of amino acids consisting of cysteine, Lysine, Histidine, Phenylalanine, Tyrosine, Glycine, Asparagine, Methionine, serine, tryptophan, Leucine, glutamine, Alanine, Isoleucine, Threonine, Proline, glutamate, Aspartate, Arginine, and Valine. Namely, in the chemical formula (I), R is the side chain of these twenty kinds of amino acids.

When the amino acid 3 is supplied to the self-assembled monolayer 2, not less than two kinds of amino acids may be supplied simultaneously. Namely, when a solution containing the amino acid 3 is supplied to the self-assembled monolayer 2, the solution may contain equal to or more than two kinds of the amino acids 3. In light of uniform bind of streptavidin to the amino acid 3, which is described later, it is preferred that the solution contains sole one kind of amino acid.

Subsequently, streptavidin 4 is supplied. The 5'-terminal amino group of the streptavidin 4 reacts with the carboxyl group of the amino acid 3. The amino group of the lysine contained in the streptavidin also reacts with the carboxyl group of the amino acid 3. Thus, two peptide bonds represented in the following chemical formula (II) are formed to obtain a sensor.

[Chem. 2]

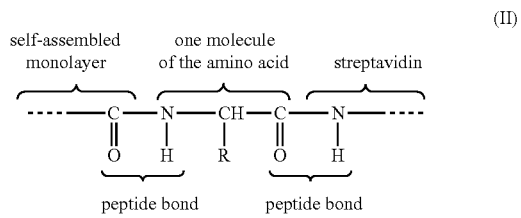

(II)

(wherein R represents a side chain of the one molecule of the amino acid)

One molecule of the streptavidin 4 has only one 5'-terminal, whereas One molecule of the streptavidin 4 has a lot of lysine group. Therefore, Almost all of the chemical formula (II) is related particularly by the following chemical formula (III).

[Chem. 3]

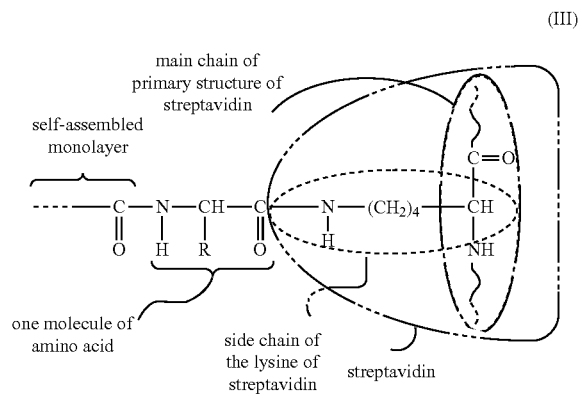

(III)

(wherein R represents a side chain of the one molecule of the amino acid)

The obtained sensor is used for detecting or quantifying the target substance contained in the sample.

Specifically, an antibody which can bind the target substance specifically is supplied to the sensor to bind the antibody to the streptavidin. Namely, the antibody is captured by the streptavidin. It is preferred that the target substance is modified with biotin, because streptavidin has high affinity to biotin. Subsequently, the sample is supplied to the sensor to cause the target substance, which is an antigen, contained in the sample to bind to the antibody.

Finally, with use of an ordinal analysis method such as Surface Plasmon Resonance (SPR) analysis method, the target substance is detected or quantified. Another analysis method such as Quarts Crystal Microbalance (QCM) may be also used.

EXAMPLES

The following examples and a comparative example describe the technologies in more detail.

Comparative Example

Figure 3:
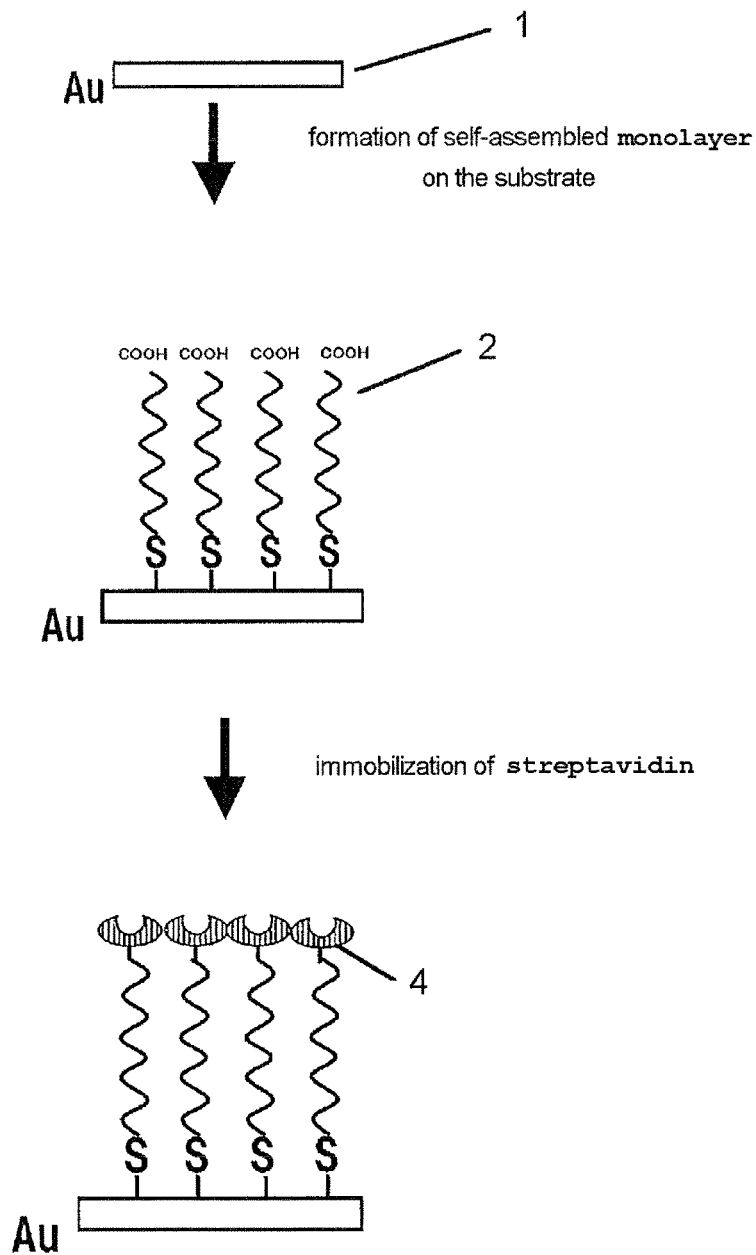
FIG. 3 shows a schematic view of a method according to the related art.

As shown in FIG. 3, a streptavidin was bound directly to a carboxyl group located at the top end of self-assembled alkanethiol formed on the gold surface with an amide coupling reaction to immobilize the streptavidin. The procedure and the results were described below.

(Preparation of a Sample Solution)

A sample solution of 16-Mercaptohexadecanoic acid with final concentration of 10 mM was prepared. The solvent thereof was ethanol.

(Formation of a Self-Assembled Monolayer)

A gold substrate (available from GE healthcare company, BR-1004-05) in which gold was vapor-deposited on glass was used as a substrate 1. The substrate 1 was washed for ten minutes with a piranha solution containing concentrated sulfuric acid and 30% hydrogen peroxide water. The volume ratio of the concentrated sulfuric acid to the 30% hydrogen peroxide water which are consisting the piranha solution was 3:1.

Subsequently, the gold substrate was immersed in the sample solution for 18 hours to form a self-assembled monolayer on the surface of the gold substrate. Finally, the substrate 1 was washed with pure water and dried.

(Immobilization of Streptavidin)

Streptavidin was bound to the carboxyl acid group located at the top end of the 16-Mercaptohexadecanoic acid which was forming the self-assembled monolayer to immobilize the streptavidin.

Specifically, the carboxyl acid group located at the top end of the 16-Mercaptohexadecanoic acid was activated with the use of 35 micro L of a mixture of 0.1M NHS(N-Hydroxysuccinimide) and 0.4M EDC (1-ethyl-3-(3-dimethylaminopropyl)carbodiimide hydrochloride). Subsequently, 35 micro L of streptavidin (250 ug/ml) was added at the flow rate of 5 micro L/minute. Thus, the carboxyl group of the 16-Mercaptohexadecanoic acid was coupled with the amino group of the streptavidin.

Example 1

Experiment was conducted similarly to the comparative example except that Glycine was supplied as the one molecule of the amino acid between the formation of the self-assembled monolayer and the immobilization of the streptavidin. The procedure and the results are described below.

(Immobilization of Amino Acid (Glycine))

Glycine was bound with the carboxyl group located at the top end of the 16-Mercaptohexadecanoic acid which formed the self-assembled monolayer 2 to immobilize the Glycine.

Specifically, after the carboxyl group had activated similar to the comparative example, 35 micro L of 0.1M Glycine (pH:8.9) was added at the flow rate of 5 micro L/minute. Thus, the carboxyl group of 16-Mercaptohexadecanoic acid was coupled with the amino group of the Glycine.

(Immobilization of Streptavidin)

Subsequently, streptavidin was bound to the carboxyl group of the Glycine to immobilize streptavidin. Specifically, after the carboxylic group of the Glycine was activated similarly to the above, 35 micro L of streptavidin (concentration: 250 micro gram/ml) was added at the flow rate of 5 micro L/minute. Thus, the carboxyl group was coupled with the 5'-terminal amino acid of the streptavidin or the amino group of the lysine contained in the streptavidin.

(Comparison of the Immobilization Amounts)

The immobilization amounts in the example 1 and the comparative example were measured with a SPR device, Biacore 3000 (available from GE healthcare company).

The term "immobilization amount" means the amount of the streptavidine immobilized per unit area.

The ratio of the immobilization amount measured in the example 1 to that of measured in the comparative example was 25.6:1.

Examples 2-20

Threonine, Methionine, Isoleucine, Proline, Serine, Glutamine, Asparagine, Phenylalanine, Tryptophan, Cysteine, Histidine, Alanine, Lysine, Leucine, Glutamate, Valine, Aspartate, Arginine, and Tyrosine were supplied respectively instead of Glycine to measure the respective immobilization amounts similarly to the example 1. These amino acids are twenty kinds of natural amino acid. Table 1 shows the measured immobilization amounts.

TABLE 1

|  | amino acid | amount |
| --- | --- | --- |
| Example 14 | Lysine | 33 |
| Example 12 | Histidine | 32.2 |
| Example 9 | Phenylalanine | 28.8 |
| Example 11 | Cysteine | 26.9 |
| Example 1 | Glycine | 25.6 |
| Example 3 | Methionine | 25.6 |
| Example 16 | Glutamate | 24.2 |
| Example 20 | Tyrosine | 24.1 |
| Example 13 | Alanine | 21.8 |
| Example 6 | Serine | 20.5 |
| Example 18 | Aspartate | 19.7 |
| Example 8 | Asparagine | 18.6 |
| Example 15 | Leucine | 12.9 |
| Example 10 | Tryptophan | 12 |
| Example 2 | Threonine | 9.1 |
| Example 4 | Isoleucine | 6.4 |
| Example 17 | Valine | 6.1 |
| Example 7 | Glutamine | 3.6 |
| Example 5 | Proline | 3.1 |
| Example 19 | Arginine | 2.5 |
| Comparative Example | (None) | 1 |

A skilled person would understand the following matters from the table 1.

When the twenty kinds of amino acids was used, the immobilization amounts increase, compared to the comparative example. Furthermore, the immobilization amount changes depending on the used amino acid.

Lysine, Histidine, Phenylalanine, Cysteine, Glycine, Methionine, Glutamate, Tyrosine, Alanine, Serine, Aspartate, Asparagine, Leucine, Tryptophan, Threonine, Isoleucine, and Valine are preferred, because each measured immobilization amounts are equal to or more than five, in case where one of these amino acids is supplied.

Lysine, Histidine, Phenylalanine, Cysteine, Glycine, Methionine, Glutamate, Tyrosine, Alanine, Serine, Aspartate, Asparagine, Leucine, and Tryptophan are more preferred, because each measured immobilization amounts are equal to or more than ten, in case where one of these amino acids is supplied.

Lysine, Histidine, Phenylalanine, Cysteine, Glycine, Methionine, Glutamate, Tyrosine, Alanine, Serine, Aspartate, and Asparagine are furthermore preferred, because each measured immobilization amounts are equal more than the average value (17.8%), in case where one of these amino acids is supplied.

Lysine, Histidine, Phenylalanine, Cysteine, Glycine, Methionine, Glutamate, Tyrosine, Alanine, and Serine are most preferred, because each measured immobilization amounts are equal to or more than twenty, in case where one of these amino acids is supplied.

INDUSTRIAL APPLICABILITY

The technologies achieve extreme increase of the amount of the streptavidin to be immobilized per unit area. This allows the sensitivity or the accuracy of the biosensor to be improved. The biosensor may be used for an inspection or a diagnosis which requires the detection or the quantification of an antigen or an antibody contained in the living sample derived from a patient at a clinical practice.

REFERENCE SIGNS LIST

1: Gold substrate
2: Alkanethiol
3: Amino Acid
4: Streptavidin

The invention claimed is:

1. A method for immobilizing a streptavidin on a self-assembled monolayer, comprising the following step (a) and step (b) in this order:

a step (a) of preparing a substrate comprising one molecule of an amino acid and the self-assembled monolayer, wherein, the one molecule of the amino acid is bound to the self-assembled monolayer through a peptide bond represented by the following chemical formula (I):

$$\underbrace{\text{-----C}}_{\text{self-assembled monolayer}} \underbrace{\overset{\text{O}}{\underset{\text{H}}{\|}} - \text{N} - \overbrace{\text{CH} - \underset{\text{R}}{|} - \overset{\text{O}}{\underset{}{\|}}\text{C} - \text{OH}}^{\text{one molecule of the amino acid}}}_{\text{peptide bond}} \quad (I)$$

wherein R represents a side chain of the one molecule of the amino acid, and wherein the one molecule of the amino acid is selected from the group consisting of Lysine, Histidine, Phenylalanine, Cysteine, Glycine, Methionine, Glutamate, Tyrosine, Alanine, Serine, Aspartate, Asparagine, Leucine, and Tryptophan, and a step (b) of supplying the streptavidin to the substrate to form a peptide bond represented by the following chemical formula (II) as a result of reaction between the carboxyl group of the one molecule of the amino acid and the amino group of the streptavidin

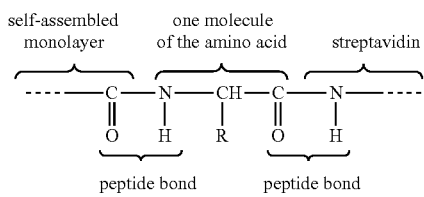

(II)

wherein R represents a side chain of the one molecule of the amino acid.

2. A method according to claim 1, wherein the step (a) comprises the following step (a1) and step (a2):
   a step (a1) of preparing a substrate comprising a self-assembled monolayer on the surface thereof, the self-assembled monolayer having a carboxylic acid at one end, and
   a step (a2) of supplying the one molecule of the amino acid to form a peptide bond represented by the chemical formula (I) as a result of reaction between the carboxylic group of the one end of the self-assembled monolayer and the amino group of the one molecule of the amino acid.

3. A method according to claim 1, further comprising the following step (ab) between the step (a) and the step (b):
   a step (ab) of activating the carboxyl group of the one molecule of the amino acid with a mixture of N-Hydroxysuccinimide and 1-ethyl-3-(3-dimethylaminopropyl)carbodiimide hydrochloride.

4. A method according to claim 2, further comprising the following step (a1a) between the step (a1) and the step (a2):
   a step (a1a) of activating the carboxyl group of the self-assembled monolayer with a mixture of N-Hydroxysuccinimide and 1-ethyl-3-(3-dimethylaminopropyl)carbodiimide hydrochloride.

5. A method according to claim 1, wherein the chemical formula (II) is represented by the following chemical formula (III)

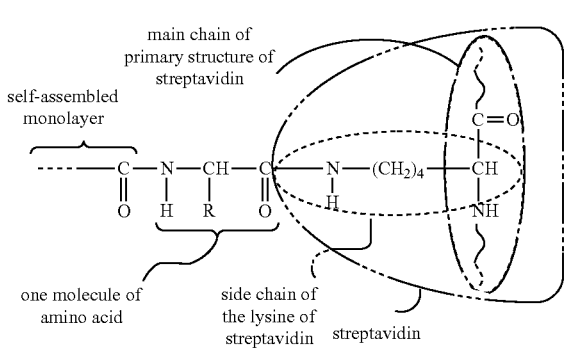

(III)

wherein R represents a side chain of the one molecule of the amino acid.

6. A method according to claim 1, wherein the one molecule of the amino acid is selected from the group consisting of Lysine, Histidine, Phenylalanine, Cysteine, Glycine, Methionine, Glutamate, Tyrosine, Alanine, Serine, Aspartate, and Asparagine.

7. A method according to claim 1, wherein the one molecule of the amino acid is selected from the group consisting of Lysine, Histidine, Phenylalanine, Cysteine, Glycine, Methionine, Glutamate, Tyrosine, Alanine, and Serine.

8. A method for detecting or quantifying a target substance contained in a sample with a sensor, comprising the following steps (a) to (d) in this order,
   a step (a) of preparing a sensor substrate comprising one molecule of an amino acid and a self-assembled monolayer, wherein, the one molecule of the amino acid is bound to the self-assembled monolayer through a peptide bond represented by the following chemical formula (I):

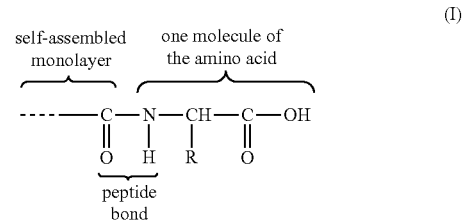

(I)

wherein R represents a side chain of the one molecule of the amino acid, and wherein the one molecule of the amino acid is selected from the group consisting of Lysine, Histidine, Phenylalanine, Cysteine, Glycine, Methionine, Glutamate, Tyrosine, Alanine, Serine, Aspartate, Asparagine, Leucine, and Tryptophan;
   a step (b) of supplying the streptavidin to the sensor substrate to form a peptide bond represented by the following chemical formula (II) as a result of reaction between the carboxyl group of the one molecule of the amino acid and the amino group of the streptavidin

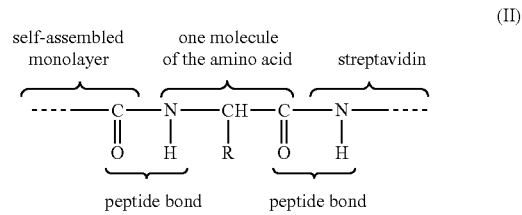

(II)

wherein R represents a side chain of the one molecule of the amino acid,
   a step (c) of supplying the sample to the sensor substrate of formula (II) to cause the target substance to bind to the streptavidin, and
   a step (d) of detecting or quantifying the target substance.

9. A method according to claim 8, wherein,
   the step (c) comprises the following steps (c1) and (c2):
   a step (c1) of binding an antibody to the streptavidin, the antibody modified with biotin, and
   a step (c2) of binding the target substance to the antibody.

10. A method according to claim 8, wherein the chemical formula (II) is represented by the following chemical formula (III)

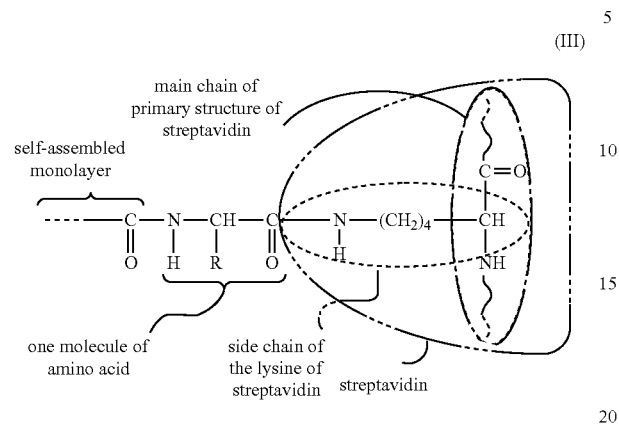

(III)

wherein R represents a side chain of the one molecule of the amino acid.

11. A method according to claim 8, wherein the one molecule of the amino acid is selected from the group consisting of Lysine, Histidine, Phenylalanine, Cysteine, Glycine, Methionine, Glutamate, Tyrosine, Alanine, Serine, Aspartate, and Asparagine.

12. A method according to claim 8, wherein the one molecule of the amino acid is selected from the group consisting of Lysine, Histidine, Phenylalanine, Cysteine, Glycine, Methionine, Glutamate, Tyrosine, Alanine, and Serine.

* * * * *